United States Patent [19]

Schmidlin

[11] 4,119,625
[45] Oct. 10, 1978

[54] PROCESS FOR THE MANUFACTURE OF STEROID CARBOXYLIC ACIDS AND THE ESTERS THEREOF

[75] Inventor: Julius Schmidlin, Basel, Switzerland

[73] Assignee: Ciba-Geigy Corporation, Ardsley, N.Y.

[21] Appl. No.: 785,997

[22] Filed: Apr. 8, 1977

[30] Foreign Application Priority Data

Apr. 15, 1976 [CH] Switzerland .................. 4848/76

[51] Int. Cl.² .............................................. C07J 71/00
[52] U.S. Cl. ......................... 260/239.55 D; 260/397.1
[58] Field of Search ................... 260/239.55 D, 397.1

[56] References Cited

U.S. PATENT DOCUMENTS

| 3,636,010 | 1/1972 | Anner et al. | 260/397.1 |
| 3,875,194 | 4/1975 | Laurent et al. | 260/397.1 |

*Primary Examiner*—Elbert L. Roberts
*Attorney, Agent, or Firm*—Theodor O. Groeger

[57] ABSTRACT

The present invention provides a novel process for the manufacture of 17- and 17a-carboxylic acids of the androstane and D-homo-androstane series respectively, of the following partial formula of the ring D

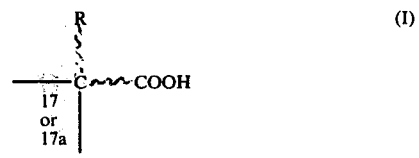

wherein R represents a hydrogen atom or an unsubstituted or substituted hydrocarbon radical or a free or functionally modified hydroxyl group, and wherein the carboxyl group can be in the α- or β-position, and of the salts and functional acid derivatives thereof, in particular their esters. The new process consists in the oxidative degradation of the side chain of corrsponding 20, 21-ketoaldehydes of the pregnane or D-homopregnane series or of the 17α-pregnane or 17aα-D-homopregnane series with an organic peracid in an inert solvent, preferably at temperatures between −20 and +30° C, and optionally converting free functional groups present into their derivatives or setting free functional groups from substituents which are derivatives of such groups.

13 Claims, No Drawings

PROCESS FOR THE MANUFACTURE OF STEROID CARBOXYLIC ACIDS AND THE ESTERS THEREOF

The present invention provides a novel process for the manufacture of 17- and 17a-carboxylic acids of the androstane and D-homo-androstane series respectively, of the following partial formula of the ring D

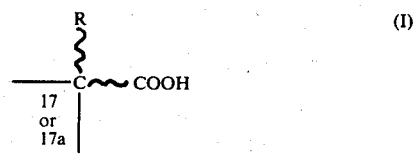

wherein R represents a hydrogen atom or an unsubstituted or substituted hydrocarbon radical or a free or functionally modified hydroxyl group, and wherein the carboxyl group can be in the α- or β-position, and of the salts and functional acid derivatives thereof, in particular their esters.

The process products are therefore 17α- or 17aβ-carboxylic acids or 17α- or 17aβ-carboxylic acids of the androstane and D-homo-androstane series respectively and the salts and functional derivatives thereof. These products include in particular both the compounds which are saturated and unsubstituted in the steroid nucleus, viz. 5α- and 5β-androstane-carboxylic acids, and those which are unsaturated and/or substituted in the nucleus in any position except in the 17- and 17a-position respectively, and their derivatives and salts as mentioned above. The compounds series referred to also include those carboxylic acids and derivatives thereof of the indicated partial formula with expanded and/or contracted A, B and/or C rings, and 18- and/or 19-nor compounds, for example carboxylic acids of gonane and oestrane compounds, or of A-nor-, A-nor-B-momo- and 5,10-seco-androstane compounds, as well as the unsaturated derivatives and/or salts and functional derivatives thereof, and their substitution products.

A functionally modified hydroxyl group R is in particular an esterified or acetalised hydroxyl group, for example one of those mentioned hereinafter. An esterified hydroxyl group R can also be in particlar a hydroxyl group which is esterified with a hydrohalic acid, i.e. a halogen atom, and as an acetalised hydroxyl group R can form an acetal group together with another hydroxyl group, for example in the 16α-position of the steroid skeleton, and with a ketone or aldehyde. A hydrocarbon radical R is in particular an alkyl group or an alkyl group which is substituted by halogen atoms. Important compounds which can be obtained by the process of the present invention are in particular the 17β-carboxylic acids of the androstane series and the derivatives thereof which contain a free, esterified or acetalised 17α-hydroxyl group and a Δ⁴-3-oxo or Δ¹,⁴-3-oxo group and an oxygen function in the 11-position, especially a 11β-hydroxyl group or an 11-oxo group, and/or optionally also halogen atoms in the 6α- and/or 9α-position and/or possibly in the 2-position, and/or a methyl or methylene group in the 16-position, in particular those compounds with an esterified 17α-hydroxyl group. The esters of such carboxylic acids with unsubstituted or substituted alcohols have a very pronounced antiinflammatory action. Compounds of this type are described for example in U.S. patent specifications Nos. 3,636,010, 3,828,080 and 3,856,828.

By functional derivatives of the 17- or 17a-carboxylic acids of the present invention are meant in particular esters. Among the salts, particular mention is to be made of the alkali metal salts or the salts of divalent ions, for example the salts of copper and zinc. Examples of 17- and 17a-carboxylic acid esters to be singled out for special mention are those which are derived from lower aliphatic alcohols, such as methyl alcohol, ethyl alcohol, propyl alcohol, isopropyl alcohol, the butyl or amyl alcohols, from araliphatic alcohols, in particular from momocyclic aryl-lower aliphatic alcohols, such as benzyl alcohol, or from heterocyclic alcohols, in particular from tetrahydropyranol or tetrahydrofuranol. They can, however, also be derived from dihydric alcohols, such as ethylene glycol or propylene glycol, or from halohydrins, for example from ethylene chlorohydrin, or from polyhydric alcohols, such as glycerol. In particular, pharmaceutically acceptable esters are prepared, for example those with good antiinflammatory action, for example those of the U.S. patents referred to above.

The preferred process for manufacturing 17α-hydroxy-steroid-17β-carboxylic acids and the derivatives thereof with functionally modified 17α-hydroxyl group, viz. especially also the pharmacologically active compounds mentioned, comprises the oxidative degradation of the 17-side-chain of corresponding 20,21-ketols of the pregnane series.

This oxidative degradation has hitherto been carried out either with periodic acid or with sodium bismuthate. However, both methods have various deficiencies. For example, when a functionally modified 17α-hydroxyl group is present, the degradation with periodic acid is unsuccessful. On the other hand, the 20,21-ketols with a free 17α-hydroxyl group are degraded by sodium bismuthate to give the corresponding 17-oxo compounds. Whilst the desired 17-carboxylic acids are obtained with this last mentioned reagent when a protected 17α-hydroxyl group is present, the yields are nonetheless unsatisfactory. The oxidation with sodium bismuthate has the further disadvantage that the reaction must be carried out in a lower aliphatic carboxylic acid in the presence of a substantial excess of the sparingly soluble oxidant - a factor which complicates the working up of the heterogeneous reaction mixture and the separation of the inorganic constituents.

It has now been found that these disadvantages can be avoided while simultaneously obtaining a greatly improved yield by using the 20,21-ketoaldehydes instead of the 20,21-ketols as starting materials and an organic peracid as oxidant.

This novel method of side-chain degradation can also be generally used for 20,21 ketoaldehydes of the pregnane and D-homopregnane series and of the corresponding 17α-pregnane and 17aα-homopregnane series, in which connection compounds with expanded and/or contracted A-, B- and/or C-rings, and/or 19-nor compounds and the derivatives which are saturated in the nucleus and the substitution products thereof are also to be classed as belonging to these series.

The process of the present invention for obtaining the carboxylic acids of the androstane and D-homo-androstane series referred to at the outset, and/or the salts and functional derivatives thereof, thus comprises oxidising corresponding 20,21-ketoaldehydes of the pregnane or D-homopregnane series or of the 17α-pregnane or 17aα-D-homopregnane series with an organic peracid in an inert solvent, and, if desired, setting free a functionally modified 17- or 17a-hydroxyl group, or functionally modifying a free 17- or 17a-hydroxyl group, and/or converting the carboxyl group into a salt or a functional derivative. The starting materials for this process are 20,21-ketoaldehydes of the pregnane, D-homopregnane, 17α-pregnane or 17aα-D-homopregnane series of the partial formula

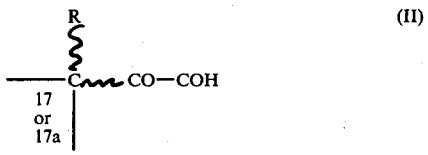 (II)

wherein R is as defined above for the process products in formula (I). The starting materials are known or can be prepared in a manner known per se, for example by oxidising the corresponding 20,21-ketols with copper-(II) salts.

A hydrocarbon radical R is — as mentioned above for the process products — preferably an alkyl group, in particular a lower alkyl group of 1 to 7 carbon atoms, primarily a methyl group. An esterified hydroxyl group R is a hydroxyl group which is esterified with an organic acid, preferably one with 2 to 10 carbon atoms, in particular with a lower aliphatic acid containing 1 to 7 carbon atoms. Such an esterified hydroxyl group is for example the acetoxy, propionyloxy, butyryloxy, valeryloxy, capronyloxy or benzoyloxy group. An acetalised hydroxyl group R is in particular the tetrahydropyranyloxy or tetrahydrofuranyloxy group.

The hydroxyl group R can form an acetyl group with an aldehyde or ketone and together with a further hydroxyl group in the steroid skeleton, for example in the 16α-position. Among the starting materials of this type, particular mention is to be made of those which have the following partial formula of the ring D

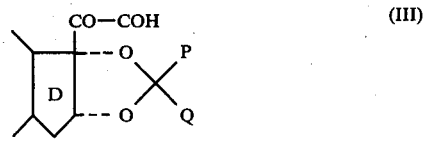 (III)

wherein each of P and Q represents a hydrocarbon radical, chiefly of aliphatic character and preferably having 1 to 7 carbon atoms, which is unsubstituted or substituted for example by halogen atoms or by free or esterified or etherified hydroxyl groups. Such a group is primarily a methyl group.

The oxidation of the starting materials is carried out by using organic peracids, in particular those commonly used in organic synthesis, for example peracetic acid, benzoic acid, monoperoxyphthalic acid, 3-chloroperoxybenzoic acid, and preferably in an inert organic solvent, for example in a lower aliphatic chlorinated hydrocarbon, such as chloroform, methylene chloride, ethylene chloride or carbon tetrachloride, in an aromatic or chlorinated aromatic hydrocarbon, such as benzene, toluene or the chlorinated derivatives thereof, such as chlorobenzene or the chlorotoluenes, or in an ether, such as a lower aliphatic ether, such as diethyl ether, or in a glycol ether, such as ethylene glycol dimethyl ether, diethylene glycol dimethyl ether, in a cyclic ether, such as dioxane or tetrahydrofurane, or in a lower aliphatic dialkylamide, for example dimethyl formamide.

The oxidation of the present process is preferably carried out at room temperature or below or optionally at slightly elevated temperature, preferably between −20° and +30° C. In general, the starting materials are treated with the peracid for approx. 1 to 24 hours.

The reaction mixture is worked up in the conventional manner by treating the excess organic peracid, optionally after adding a diluent, with a solution of sodium iodide and thereafter with a solution of sodium thiosulphate. To separate the process product from the carboxylic acid formed as by-product by reduction of the peracid, it is advantageous to esterify the resultant acid mixture, to separate the steroid ester from the ester of the reduced reagent on the basis of the ready solubility and low polarity of the latter by simple crystallisation and/or by short chromatography, and, if appropriate, to recover the free acid from the isolated steroid carboxylic acid ester.

If desired, a 17- or 17a-hydroxyl group which is present in the steroid carboxylic acids in functionally modified form, for example in esterified or acetalised form, can be sset free in known manner. Thus, for example, an esterified 17- or 17a-hydroxyl group can be set free by treatment with a base, such as an alkali hydroxide.

A free 17- or 17a-hydroxyl group which is present in the process products can be functionally modified in a manner known per se, for example esterified or acetalised. Esterification is effected by treatment with, for example, a carboxylic acid anhydride or carboxylic acid chloride, optionally in the presence of a base. Thus, if desired, a hydroxyl group which is for example in the 17α-position is esterified by treatment with a carboxylic acid anhydride in the presence of a strong acid, such as p-toluenesulphonic acid or perchloric acid, or with an acid ion exchanger, such as Amberlite IR 120, or sulphosalicyclic acid and, most advantageously, in the presence of trifluoroacetic acid anhydride. The reaction is advantageously carried out in a hydrocarbon, such as benzene or toluene, or in a chlorinated aliphatic hydrocarbon, such as methylene chloride or chloroform. Suitable acylating agents are also acid chlorides or bromides, in which case esterification can also be carried out in the presence of a base, such as pyridine, and at low temperature, for example at 0° C.

It is also possible to obtain 17α-esters from 17α-hydroxysteroid-17β-carboxylic acids in such a way that these latter are reacted initially with the anhydride corresponding to the ester group to be introduced, when the 17-ester of the mixed anhydride of the acid in question and of the steroid-17-carboxylic acid is formed. The reaction is preferably carried out at elevated temperature. The mixed anhydride can subseuqently be resolved by solvolysis, for example by treatment with basic or alkaline media, for example with aqueous acetic acid or aqueous pyridine or diethylamine in acetone.

The acetalising of a 17- or 17a-hydroxyl group is accomplished in a manner known per se. For example, a tetrahydropyranol- or tetrahydrofuranylacetal is prepared by treatment with dihydropyrane or dihydrofurane in the presence of phosphoroxy chloride. A 16,17-ketal or acetal is prepared for example by reacting a 16α,17α-dihydroxy group with the relevant ketone or aldehyde in the presence of a strong acid in a manner known per se.

The optional setting free of acetal groups R in the process products can also be carried out in a manner known per se, for example by acid hydrolysis.

The optional conversion of the resultant 17- or 17a-androstane-carboxylic acids into their functional derivatives can be carried out in a manner known per se. For example, the free acid is used as starting material and reacted with a reactive functional derivative of the respective alcohol, such as an alkyl halide, for example an alkyl bromide or alkyl chloride, or a dialkyl sulphate, such as dimethyl sulphate, in the presence of a base, such as pyridine or sodium hydroxide solution, or the reaction is carried out direct with the alcohol with the addition of a dehydrating agent, such as sulphuric acid or hydrogen chloride or zinc chloride. The reaction with diazomethane is particularly suitable for obtaining the methyl ester. Finally, the acid can also be converted into the corresponding acid chloride or bromide, which is reacted with the desired alcohol.

If a metal salt of the above mentioned acids is used as starting material, in particular an alkali metal salt, then in accordance with the process the esters are prepared by reaction with a halogenated hydrocarbon, such as an alkyl halide, for example methyl bromide, ethyl chloride or benzyl chloride, in a manner known per se.

The 20,21-ketols of the pregnane, 17α-pregnane, D-homopregnane and 17aα-D-homopregnane series which are required for the present process are known or they can be obtained in a manner known per se.

The invention also relates to those embodiments of the process in which a compound obtainable at any stage of the process is used as starting material and the missing steps are carried out, or the process is interrupted at any stage, or in which a starting material is formed under the reaction conditions.

The invention is illustrated in more detail by the following Examples.

EXAMPLE 1

8 ml of a 0.05 M solution of copper(II) acetate in methanol are added to a solution of 466.6 mg of 6α,9α-difluoro-11β,21-dihydroxy-16α-methyl-17α-propionyloxy-pregna-1,4-diene-3,20-dione in 32 ml of methanol and oxygen is introduced, with stirring, over the course of 2 hours. The reaction mixture is thereafter treated with 8 ml of a 0.05 M aqueous solution of disodium ethylenediaminetetraacetate and the methanol is removed by distillation at 3 to 5 torr while adding 36 ml of water. After concentrating the batch to approx. 4 ml, the precipitated crystals of 6α,9α-difluoro-11β-hydroxy-16α-methyl-3,20-dioxo-17α-propionyloxy-pregna-1,4-diene-21-al are collected on a filter, washed with a small amount of ice-cold water and dried in vacuo over calcium chloride. The resultant 512 g of crude aldehyde are dissolved in 12.5 ml of dichloromethane. Then 1 g of 3-chloro-peroxybenzoic acid (content: approx. 90%) is added and the reaction mixture is stirred for 1 hour at 23°-25° C., subsequently diluted with 100 ml of ether and 12.5 ml of dichloromethane, extracted in succession with a mixture of 30 ml of a 0.4 M solution of sodium iodide and 10 ml of 2N sulphuric acid, then with 20 ml of a 0.5N solution of sodium thiosulphate and a total of 60 ml of water. The aqueous extracts are extracted with a 1:4 mixture of dichloromethane and ether. The combined organic phases are dried over sodium sulphate and evaporated in vacuo to yield 1.422 g of crystalline residue consisting of 6α,9α-difluoro-11β-hydroxy-16α-methyl-3-oxo-17α-propionyloxy-androsta-1,4-diene-17-carboxylic acid, and, as by-product, 3-chlorobenzoic acid. To separate the 3-chlorobenzoic acid, the resultant mixture is esterified for example with diazomethane and the steroid carboxylic acid is isolated as the methyl ester as follows:

1.442 g of the above acid mixture is dissolved in 25 ml of dichloromethane and 15 ml of ether. The solution is cooled to 0°-3° C. and, in the course of 15 minutes, 20 ml of approx. 0.8M diaxomethane in ether are added thereto. The reaction solution is thereafter concentrated under reduced pressure and while repeatedly adding ether to yield 498 g of crystals from which, after chromatography over silica gel with chloroform/methanol (99:1) as eluant, 317 mg of methyl 6α,9α-difluoro-11β-hydroxy-16α-methyl-3-oxo-17α-propionyloxy-17-carboxylate with a melting point of 275°-278° C. are obtained.

EXAMPLE 2

6.25 ml of a 0.05 M solution of copper (II) acetate in methanol are added to a solution of 566 mg of 6α,9α-difluoro-11β-dihydroxy-16α,17α-isopropylidenedioxy-pregna-1,4-diene-3,20-dione in 25 ml of methanol and the reaction mixture is stirred for 4 hours while introducing oxygen. The blue solution is then cooled to 0° C., 6.25 ml of a 0.05 M aqueous solution of disodium ethylenediaminetetraacetate are added and, while adding 12.5 ml of water, the batch is subsequently concentrated to a residual volume of approx 5 ml. The 603 mg of 6α,9α-difluoro-11β-hydroxy-16α,17α-isopropylidenedioxy-3,20-dioxo-pregna-1,4-diene-21-al, obtained after suction filtration and drying, are dissolved in 12.5 ml of dichloromethane. Then 1.25 g of 3-chloro-peroxybenzoic acid (content: approx. 90% are added and the mixture is stirred for 6 hours at 20°-23° C. The reaction solution is then diluted with 162.5 ml of ether and 25 ml of dichloromethane and, after addition of 25 g of crushed ice, extracted firstly with a mixture of 75 ml of a 0.2 M solution of sodium iodide and 12.5 ml of 2 N sulphuric acid, thereafter with 62.5 ml of 0.2 N sodium thiosulphate solution, and finally with water. The aqueous extracts are extracted with a 1:4 mixture of dichloromethane and ether. The combined organic phases are dried over sodium sulphate and concentrated under reduced pressure to yield 2.015 g of crystalline residue consisting of 6α,9α-difluoro-11β-hydroxy-16α,17α-isopropylidene-dioxy-3-oxo-androsta-1,4-diene-17β-carboxylic acid and, as by-product, 3-chlorobenzoic acid. To separate the 3-chlorobenzoic acid, the resultant mixture is esterified for example with diazomethane and the steroid carboxylate is isolated as the methyl ester as follows:

The 2.015 g of the mixture of acids are dissolved in 50 ml of ether and the solution, which is cooled to 0° C., is treated in the course of 15 minutes with 17.5 ml of an approx. 0.5 M solution of diaxomethane in ether. After it has been stirred for a further one and a half hours at 0° C., the solution is highly concentrated under reduced pressure, whereupon altogether 602.5 mg of crude methyl ester precipitate while cautiously adding petroleum ether at low temperature. Chromatography of the methyl ester through 50 times its weight of silica gel with chloroform/methanol (99:1) as eluant and recyrstallisation of the crystalline fractions from methanol yields a total of 429 mg of pure methyl 6α,9α-difluoro-11β-hydroxy-16α,17α-isopropylidenedioxy-3-oxo-androsta-1,4-diene-17β-carboxylate with a melting point of 308°-314° C.

EXAMPLE 3

A 0.05 M solution of copper(II) acetate in methanol (5 ml) is added to a solution of 486.5 mg of 2-chloro-6α,-9α-difluoro-11β,21-dihydroxy-16α,17α-isopropylidenedioxy-pregna-1,4-diene-3,20-dione in 20 ml of methanol and then oxygen is introduced, with stirring, over the course of 4 hours at room temperature. The reaction mixture is subsequently cooled to approx. 3° C., 5 ml of a 0.05 M aqueous solution of disodium ethylenediaminetetraacetate are added and the methanol is removed in vacuo. The residue is diluted with 7 ml of water and the crystalline crude product is separated from the aqueous phase by washing with ice-cold water and dried in vacuo to yield 447 mg of 2-chloro-6α,9α-difluoro-11β-hydroxy-16α,17α-isopropylidene-dioxy-3,20-dioxo-pregna-1,4-diene-21-al. This aldehyde (400 mg) is dissolved in 8 ml of dichloromethane and, after addition of 820 mg of 3-chloro-peroxybenzoic acid (content: approx. 90%), the reaction mixture is allowed to stand for 6 hours at normal temperature and then diluted with an abundant amount of chloroform. The solution is washed in succession with a solution of sodium iodide acidified with sulphuric acid, sodium thiosulphate solution, and water, dried over sodium sulphate, and concentrated in vacuo. The residual crystalline residue weighs 1 g and consists of 2-chloro-6α,9α-difluoro-11β-hydroxy-16α,17α-isopropylidenedioxy-3-oxo-androsta-1,4-diene-17β-carboxylic acid and, as by-product, 3-chlorobenzoic acid.

To separate the 3-chlorobenzoic acid, the resultant mixture of acids is reacted with diazomethane and the steroid carboxylic acid is isolated as the methyl ester, for example as follows: The mixture of acids is dissolved in 10 ml of methanol and the solution is treated at room temperature with 30 ml of an approx. 0.6 M solution of diazomethane in ether. After 20 minutes the reaction solution is concentrated in vacuo and the residue is chromatographed over 100 g of silica gel using 95:5, 92:8 and 90:10 mixtures of toluene/ethyl acetate. Recrystallisation of the crystalline eluates from methanol/ether using dichloromethane as hydrotropic agent yields 148 mg of pure methyl 2-chloro-6α,9α-difluoro-11β-hydroxy-16α,17α-isopropylidenedioxy-3-oxo-androsta-1,4-diene-17β-carboxylate with a melting point of 289°–290° C.

I claim:

1. A process for the manufacture of steroid carboxylic acids selected from the group consisting of those having the formula 1

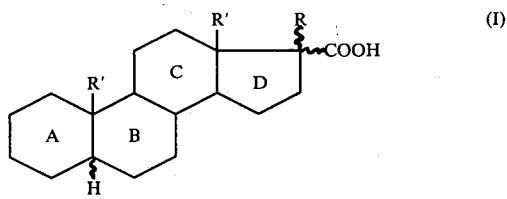

wherein R represents a hydrogen atom, an unsubstituted or substituted hydrocarbon radical, or a free or conventionally esterified or etherified hydroxyl group, and wherein the carboxyl group and the 5H-atom can be in the alpha or beta position, R ' represents hydrogen or methyl, and its derivatives having expanded or contracted A-, B-and C-rings, an expanded D-ring having R and COOH in 17a-position, one or more than one double bond and/or conventional steroid-substituents in any of the positions different from 17 or 17a; which process comprises oxidising a corresponding 20,21-ketoaldehyde having the group CO-CHO instead of COOH in said 17- or 17a-positions, wih an organic peracid in an inert solvent.

2. A process according to claim 1, wherein peracetic acid, perbenzoic acid, monoperoxyphthalic acid or 3-chloroperoxy-benzoic acid is used as organic peracid.

3. A process according to claim 1, wherein a lower aliphatic chlorinated hydrocarbon, an aromatic or chlorinated aromatic hydrocarbon, an ether or a lower aliphatic dialkylamide is used as inert solvent.

4. A process according to claim 1, wherein the oxidation with the peracid is carried out at temperatures between −20° and +30° C.

5. A process according to claim 1, wherein the starting materials are compounds of the pregnane or D-homopregnane series.

6. A process according to claim 5, wherein the starting material is said pregnane or D-homopregnane in which R represents an esterified or acetalised hydroxyl group.

7. A process according to claim 5, wherein the starting material is said pregnane or D-homopregnane with the following partial formula of the ring D

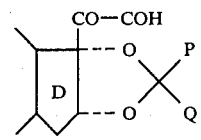

wherein P and Q individually or together represent a hydrocarbon radical, containing 1 to 7 carbon atoms, which is unsubstituted or substituted by halogen atoms, free hydroxyl groups or by esterified or etherified hydroxyl groups.

8. A process according to claim 1, wherein a starting material of the formula

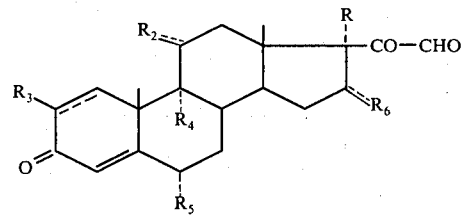

is used
wherein R has the same meaning as in claim 1, $R_2$ is a hydroxy or an oxo group, any of the substituents $R_3, R_4$, and $R_5$ represents hydrogen or halogen, $R_6$ represents 2 hydrogen atoms or hydrogen togehter with a methyl group in either the alpha- or beta-position, or a methylene group or, together with R, a hydrogen atom together with a 16alpha, 17alpha-dihydroxy-acetonide grouping; or the 1,2-dehydro derivative thereof.

9. A process according to claim 8, which comprises the use of said starting material wherein R is an esterified hydroxyl group.

10. A process according to claim 1, wherein resultant carboxylic acids of formula I are converted into their conventional salts or esters.

11. A process according to claim 1, wherein the resultant carboxylic acids of formula I are converted into their conventional esters, which latter are isolated and re-converted into the carboxylic acids of formula I.

12. A process according to claim 1, wherein in any resultant carboxylic acid of formula I with R being a free hydroxyl group, the latter is converted into a conventionally estrified or acetalised hydroxyl group.

13. A process according to claim 1, wherein in any resultant carboxylic acid of formula I with R being an esterified or acetalised hydroxyl group, the latter is converted into a free hydroxyl group.

* * * * *